United States Patent
Emerson et al.

(10) Patent No.: US 9,295,405 B2
(45) Date of Patent: Mar. 29, 2016

(54) SV/CO TRENDING VIA INTRACARDIAC IMPEDANCE

(75) Inventors: Paul F. Emerson, St. Louis Park, MN (US); Pramodsingh Hirasingh Thakur, White Bear Lake, MN (US); Yan Zou, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 933 days.

(21) Appl. No.: 13/432,619

(22) Filed: Mar. 28, 2012

(65) Prior Publication Data

US 2012/0271177 A1 Oct. 25, 2012

Related U.S. Application Data

(60) Provisional application No. 61/478,683, filed on Apr. 25, 2011.

(51) Int. Cl.
*A61B 5/08* (2006.01)
*A61B 5/053* (2006.01)
*A61B 5/0205* (2006.01)
*A61B 5/029* (2006.01)
*A61N 1/365* (2006.01)
*A61N 1/372* (2006.01)
*A61N 1/362* (2006.01)
*A61B 7/00* (2006.01)
*A61B 5/00* (2006.01)
*A61B 5/0215* (2006.01)

(52) U.S. Cl.
CPC .............. *A61B 5/0538* (2013.01); *A61B 5/0031* (2013.01); *A61B 5/0205* (2013.01); *A61B 5/029* (2013.01); *A61N 1/3622* (2013.01); *A61N 1/3627* (2013.01); *A61N 1/36521* (2013.01); *A61N 1/36542* (2013.01); *A61N 1/37247* (2013.01); *A61N 1/37258* (2013.01); *A61N 1/37282* (2013.01); *A61B 5/0215* (2013.01); *A61B 5/7239* (2013.01); *A61B 7/00* (2013.01)

(58) Field of Classification Search
USPC .................................. 600/484, 483, 508, 528
See application file for complete search history.

(56) References Cited

U.S. PATENT DOCUMENTS

| | | |
|---|---|---|
| 4,674,518 A | 6/1987 | Salo |
| 4,686,987 A | 8/1987 | Salo et al. |
| 6,278,894 B1 | 8/2001 | Salo et al. |
| 7,603,170 B2 | 10/2009 | Hatlestad et al. |

(Continued)

OTHER PUBLICATIONS

Abraham, William T, et al., "Prospective Evaluation of Cardiac Decompensation in Patients with Heart Failure by Impedance Cardiography Test: The PREDICT Multicenter Trial", Circulation, 110(suppl III), (2004), 12 pgs.

(Continued)

*Primary Examiner* — Michael Kahelin
*Assistant Examiner* — Mitchell E Alter
(74) *Attorney, Agent, or Firm* — Schwegman Lundberg & Woessner, P.A.

(57) ABSTRACT

A patient-specific model can show changes in cardiac stroke volume or cardiac output, such as to predict heart failure or to indicate cardiac remodeling. The patient-specific model can be derived from a surrogate indication of a cardiac stroke volume, such as a physical activity level, and features obtained from a thoracic impedance waveform, such as mean or peak-to-peak impedance values. In an example, several models corresponding to different patient physical activity levels can be determined.

19 Claims, 8 Drawing Sheets

(56) References Cited

U.S. PATENT DOCUMENTS

| | | | |
|---|---|---|---|
| 7,640,056 | B2 | 12/2009 | Belalcazar |
| 7,751,889 | B1 | 7/2010 | Schecter |
| 2002/0045809 | A1* | 4/2002 | Ben-Haim .................. 600/374 |
| 2002/0161410 | A1* | 10/2002 | Kramer et al. .................. 607/9 |
| 2007/0066905 | A1 | 3/2007 | Zhang |
| 2010/0004714 | A1* | 1/2010 | Georgakopoulos et al. .... 607/44 |
| 2010/0016915 | A1 | 1/2010 | Blomqvist et al. |
| 2011/0152963 | A1 | 6/2011 | Stahmann et al. |
| 2012/0165884 | A1* | 6/2012 | Xi et al. ............................ 607/4 |

OTHER PUBLICATIONS

Albert, Nancy M, et al., "Evidence-Based Practice for Acute Decompensated Heart Failure", Critical Care Nurse, 24, (2004), 14-29.

Balasubramanian, V. et al., "Electrical impedance cardiogram in derivation of systolic time intervals", British Heart Journal, 40, (1978), 268-275.

Critchley, Lester A. H., et al., "The Effect of Peripheral Resistance on Impedance Cardiography Measurements in the Anesthetized Dog", Anesth Analg., 100(6), (2005), 1708-12.

Gadler, F., et al., "Long-Term Changes in Intracardiac Impedance in Cardiac Resynchronization Therapy Patients", Journal of Cardiac Failure, 16(8), Supplement, Abstracts From the 14th Annual Scientific Meeting Heart Failure Society of America Sep. 12-15, 2010, (Aug. 2010), S68.

Grubb, Blair P, et al., "Adaptive Rate Pacing Controlled by Right Ventricular Preejection Interval for Severe Refractory Orthostatic Hypotension", Pacing Clin Electrophysiol., 16(4 Pt 1), (1993), 801-5.

Hoetink, A E, et al., "On the Flow Dependency of the Electrical Conductivity of Blood", IEEE Transactions on Biomedical Engineering, 51(7), (Jul. 2004), 1251-1261.

Izakovic, M, "Central venous pressure—evaluation, interpretation, monitoring, clinical implications", Bratisl Lek Listy, 109(4), (2008), 187-187.

Joseph, Susan M, "Acute Decompensated Heart Failure", Texas Heart Institute Journal, 36(6), (2009), 510-520.

Lababidi, Zuhdi, et al., "The First Derivative Thoracic Ipedance Cardiogram", Circulation, 41(4), (1970), 651-8.

Matsuno, Y, et al., "Mechanism of Prolongation of Pre-ejection Period in the Hypertrophied Left Ventricle with Normal Systolic Function in Unanesthetized Hypertensive Dogs", Clin Cardiol., 11(10), (1988), 702-6.

Patangay, Abhilash, et al., "Heart Sounds Based Measures of Cardiac Status for Heart Failure Patient Management", 31st Annual International Conference of the IEEE EMBS Minneapolis, Minnesota, USA, Sep. 2-6, 2009, (2009), 4 pgs.

Ruiter, J H, et al., "Adaptive Rate Pacing Controlled by the Right Ventricular Preejection Interval: Clinical Experience With a Phyiological Pacing System", Pacing Clin Electrophysiol., 15(6), (Jun. 1992), 886-94.

Salo, Rodney, et al., "Chapter 13: The Use of Intracardiac Impedance-Based Indicators to Optimize Pacing Rate", Clinical Cardiac Pacing, Philadelphia: WB Saunders; Ellenbogen KA, Kay GN, Wilkoff BL, editors., (1995), 233-249.

Salo, Rodney, "Experience with the PRECEPT Impedance Controlled Pacemaker Abstract", In proc. of the 1st World Congress on Biomimetics and Artificial Muscles, Albuquerque, New Mexico, Dec. 2002., Abstract, (2002), 1 pg.

Schreckenberg, Marcus, et al., "High-Resolution Transthoracic Real-Time Three-Dimensional Echocardiography Quantitation of Cardiac Volumes and Function Using Semi-Automatic Border Detection and Comparison With Cardiac Magnetic Resonance Imaging", Journal of the American College of Cardiology, 43(11), (2004), 2083-2090.

Stinstra, Jeroen G, at al., "On the Passive Cardiac Conductivity", Annals of Biomedical Engineering, 33(12), (Dec. 2005), 1743-1751.

Valzania, Cinzia, et al., "Multiple Vector Impedance Measurements During Biventricular Pacing: Feasibility and Possible Implications for Hemodynarnic Monitoring", Pacing Clin Electrophysiol., 32(12), (Dec. 2009), 1492-500.

Visser, K R, "Electric conductivity of stationary and flowing human blood at low frequencies", Med & Biol. Eng. & Comput, 30, (1992), 636-640.

Wortel, Hetty, et al., "Impedance Measurements in the Human Right Ventricle Using a New Pacing System", Pacing Clin Electrophysiol., 14(9), (Sep. 1991), 1336-42.

\* cited by examiner

FIG. 9A

| | | VECTOR 1 | | | VECTOR 2 | | | VECTOR 3 | | |
|---|---|---|---|---|---|---|---|---|---|---|
| MEAN PHYSICAL ACTIVITY LEVEL | HEART RATE | $I_{PEAK-TO-PEAK}$ | $I_{MEAN}$ | $\frac{I_{PEAK-TO-PEAK} * I_{MEAN}}{}$ | $I_{PEAK-TO-PEAK}$ | $I_{MEAN}$ | $\frac{I_{PEAK-TO-PEAK} * I_{MEAN}}{}$ | $I_{PEAK-TO-PEAK}$ | $I_{MEAN}$ | $\frac{I_{PEAK-TO-PEAK} * I_{MEAN}}{}$ |
| RANGE 1 | HR1 | $P_{1-VECTOR1}$ | $M_{1-VECTOR1}$ | $X_{1-VECTOR1}$ | $P_{1-VECTOR2}$ | $M_{1-VECTOR2}$ | $X_{1-VECTOR2}$ | $P_{1-VECTOR3}$ | $M_{1-VECTOR3}$ | $X_{1-VECTOR3}$ |
| RANGE 2 | HR2 | $P_{2-VECTOR1}$ | $M_{2-VECTOR1}$ | $X_{2-VECTOR1}$ | $P_{2-VECTOR2}$ | $M_{2-VECTOR2}$ | $X_{2-VECTOR2}$ | $P_{2-VECTOR3}$ | $M_{2-VECTOR3}$ | $X_{2-VECTOR3}$ |
| RANGE 3 | HR3 | $P_{3-VECTOR1}$ | $M_{3-VECTOR1}$ | $X_{3-VECTOR1}$ | $P_{3-VECTOR2}$ | $M_{3-VECTOR2}$ | $X_{3-VECTOR2}$ | $P_{3-VECTOR3}$ | $M_{3-VECTOR3}$ | $X_{3-VECTOR3}$ |
| RANGE 4 | HR4 | $P_{4-VECTOR1}$ | $M_{4-VECTOR1}$ | $X_{4-VECTOR1}$ | $P_{4-VECTOR2}$ | $M_{4-VECTOR2}$ | $X_{4-VECTOR2}$ | $P_{4-VECTOR3}$ | $M_{4-VECTOR3}$ | $X_{4-VECTOR3}$ |
| RANGE 5 | HR5 | $P_{5-VECTOR1}$ | $M_{5-VECTOR1}$ | $X_{5-VECTOR1}$ | $P_{5-VECTOR2}$ | $M_{5-VECTOR2}$ | $X_{5-VECTOR2}$ | $P_{5-VECTOR3}$ | $M_{5-VECTOR3}$ | $X_{5-VECTOR3}$ |

FIG. 9B

| | SUBJECT 1 | SUBJECT 2 | SUBJECT 3 | SUBJECT 4 | SUBJECT 5 | SUBJECT 6 | SUBJECT 7 | SUBJECT 8 |
|---|---|---|---|---|---|---|---|---|
| $K1 * M_{[n]-VECTOR2}$ | 13.78 | -0.08 | -0.06 | -5.52 | 9.97 | -10.72 | -1.50 | -3.51 |
| $K2 * M_{[n]-VECTOR3}$ | -13.93 | 0.07 | -0.12 | 5.68 | -9.81 | 10.66 | 1.64 | 3.77 |
| $K3 * P_{[n]-VECTOR1}$ | 1.57 | 1.07 | 0.40 | -0.17 | -2.39 | 1.86 | 0.18 | 0.58 |
| K4 | -144.60 | 6.70 | 94.64 | 34.30 | -133.67 | 192.79 | -26.13 | -60.30 |

902

| | | | | |
|---|---|---|---|---|
| 1 FEATURE | $P_{[n]}$-VECTOR 1 | | | 0.791 |
| | $X_{[n]}$-VECTOR 2 | | | 0.746 |
| | $M_{[n]}$-VECTOR 3 | | | 0.730 |
| 2 FEATURES | $P_{[n]}$-VECTOR 1 | $M_{[n]}$-VECTOR 1 | | 0.854 |
| | $M_{[n]}$-VECTOR 2 | $X_{[n]}$-VECTOR 2 | | 0.853 |
| | $P_{[n]}$-VECTOR 1 | $M_{[n]}$-VECTOR 3 | | 0.844 |
| 3 FEATURES | $M_{[n]}$-VECTOR 1 | $M_{[n]}$-VECTOR 2 | $X_{[n]}$-VECTOR 3 | 0.910 |
| | $P_{[n]}$-VECTOR 1 | $M_{[n]}$-VECTOR 1 | $X_{[n]}$-VECTOR 1 | 0.907 |
| | $X_{[n]}$-VECTOR 2 | $P_{[n]}$-VECTOR 3 | $M_{[n]}$-VECTOR 3 | 0.907 |

911 – 1 FEATURE rows
912 – 2 FEATURES rows
913 – 3 FEATURES rows

SV/CO TRENDING VIA INTRACARDIAC IMPEDANCE

CLAIM OF PRIORITY

This application claims the benefit of priority under 35 U.S.C. §119(e) of Thakur et al., U.S. Provisional Patent Application Ser. No. 61/473,349, entitled "SV/CO TRENDING VIA INTRACARDIAC IMPEDANCE", filed on Apr. 25, 2011, which is herein incorporated by reference in its entirety.

BACKGROUND

A medical device can be implanted in a body to perform one or more tasks including monitoring, detecting, or sensing physiological information in or otherwise associated with the body, diagnosing a physiological condition or disease, treating or providing a therapy for a physiological condition or disease, or restoring or otherwise altering the function of an organ or a tissue. Examples of an implantable medical device can include a cardiac rhythm management device, such as a pacemaker, a cardiac resynchronization therapy device, a cardioverter or defibrillator, a neurological stimulator, a neuromuscular stimulator, or a drug delivery system, among others.

Cardiac rhythm or function management devices can be configured to sense cardiac activity, deliver pacing pulses to evoke responsive heart contractions, or deliver a shock to interrupt certain arrhythmias. In certain examples, one or more of these functions can help improve a patient's cardiac rhythm, such as including improving cardiac output of blood to help meet a patient's metabolic need for such cardiac output. In other examples, cardiac function or other physiological patient variables can be monitored, such as to provide an indication of a worsening or improving cardiac disease status. In some examples, a pacing rate can be adapted in accordance with metabolic rate or demand.

Many variables can indirectly reflect a body's metabolic rate, including body temperature, ventilation rate, minute ventilation, or cardiac output. Minute ventilation, for example, varies almost linearly with aerobic oxygen consumption during exercise, and it is a commonly-used variable in rate-adaptive pacemakers to reflect the exertion level of the patient. Cardiac output, a key indicator of cardiac function, is a function of heart rate and cardiac stroke volume, or the volume of blood that can be pumped from one ventricle during a cardiac cycle. Other, more indirect indications of metabolic rate can include a body physical activity level, such as can be measured using an accelerometer. Physical activity is correlated with metabolic demand because such activity requires energy expenditure and oxygen consumption.

Information about a stroke volume can provide an indication of a patient cardiac status. For example, in a heart failure patient, a decrease in stroke volume over several days can indicate an increased risk for a decompensation episode. Various methods of trending heart failure have been proposed, including using thoracic impedance information. For example, Blomqvist et al., in U.S. Patent Publication No. 2010/0016915, entitled "MEDICAL DEVICE AND SYSTEM FOR DETERMINING A HEMODYNAMIC PARAMETER USING INTRACARDIAC IMPEDANCE," refers to using hemodynamic status information in the extreme point sections of an impedance morphology curve. Some methods can be adapted to individual patients. Valzania et al., in Vol. 32, December, 2009, of Pacing and Clinical Electrophysiology, entitled "MULTIPLE VECTOR IMPEDANCE MEASUREMENTS DURING BIVENTRICULAR PACING: FEASIBLITY AND POSSIBLE IMPLICATIONS FOR HEMODYNAMIC MONITORING" refers to using multiple impedance signals to monitor hemodynamic variables in heart failure patients, and monitoring heart function using relative, intra-individual variations in intracardiac impedance.

Stroke volume can indicate other cardiac conditions. For example, low stroke volume can indicate a tachyarrhythmia. Increased stroke volume, such as over several weeks or months, can indicate beneficial cardiac remodeling. Stroke volume can also indicate a need for therapy. For example, the PRECEPT pacemaker, designed by Guidant/Cardiac Pacemakers, Inc. and under clinical investigation from 1989-1992, used relative stroke volume information derived from intracardiac impedance measurements to control pacing rate.

Stroke volume can be determined using a variety of methods, including indirect methods. For example, systolic time intervals can be used to indicate a surrogate for stroke volume. Systolic time intervals, such as PEP or LVET, can be inferred from the timings of peaks in the first derivative of a thoracic impedance waveform, dZ/dt. In another example, systolic time intervals can be inferred from timings of S1 and S2 heart sounds. Some methods used to predict and trend cardiac stroke volume use implanted electrodes in a known, fixed geometry. Some of these methods use single predictors, such as a change in peak-to-peak amplitude in a right ventricular intracardiac impedance, to monitor stroke volume.

Overview

Various electrical or mechanical functions of the heart can provide a variety of physiological parameters that can indicate the onset of a condition, for instance, heart failure, arrhythmia(fibrillation, tachycardia, bradycardia), ischemia, or the like. These physiological parameters can include, for example, heart sounds (e.g., S3 amplitude), DC impedance near the lungs, heart rate, respiration rate, or intracardiac pressure. Further examples of a physiological parameter can include, but are not limited to, a hormone level, a blood count, a neural activity, a physical activity, or any other physiological parameter. At least some of these parameters can be used to provide an indication of a cardiac stroke volume, and can be used to indicate the onset or change of a condition.

Cardiac stroke volume information can be monitored and used to provide an alert that therapy (or therapy adjustment) is needed, such as defibrillation, change in pacing, or the like. It can be difficult, however, to provide a reliable indication of a cardiac stroke volume in each patient over time where several variables, including unique patient physiology and electrode lead geometry, can complicate a direct measure of stroke volume. Furthermore, as heart morphology changes, such as due to heart failure, a single-predictor cardiac stroke volume model may not be effective. Adding a second or third predictor can compensate for this variability and better predict cardiac stroke volume, or a surrogate for cardiac stroke volume.

Multiple predictors can be derived from one or more thoracic impedance vectors to predict and trend cardiac stroke volume in an individual patient, and the multiple predictors can be unique to each patient. The multiple predictors can be used to form a patient-specific model for cardiac stroke volume. The model can be used in a predictive sense to identify a cardiac status. Because stroke volume trending can be relative to an individual patient baseline, precise stroke volume measurements are not required.

This document describes, among other things, systems, methods, machine-readable media, or other techniques that can involve receiving reference physiological information, deriving a model for cardiac stroke volume that can be used in a predictive sense, receiving test physiological information, and applying the test physiological information to the model to obtain an indication of a cardiac stroke volume. The techniques can involve obtaining thoracic impedance information, such as a waveform, and obtaining a surrogate indication of a cardiac stroke volume, such as a physical activity level. The techniques can involve trending cardiac stroke volume.

The techniques described and illustrated herein can be directed toward diagnosing a patient risk for cardiac decompensation in advance of heart failure, providing an indication of beneficial cardiac remodeling, or discriminating between lethal and non-lethal cardiac arrhythmias.

The present inventors have recognized, among other things, that a problem to be solved can include identifying patients at imminent or immediate risk of a decompensation or heart failure event. The present inventors have recognized that another problem to be solved can include inhibiting unnecessary delivery of defibrillation energy, and discriminating between several cardiac arrhythmias. In an example, the present subject matter can provide a solution to these problems, such as by receiving, during a stable patient state, reference information including a thoracic impedance waveform and a surrogate indication of cardiac stroke volume. The reference information can be used to determine a patient-specific model that can provide a cardiac status indication using the surrogate indication of cardiac stroke volume and features extracted from the thoracic impedance waveform. During a trending or test period, test impedance information can be acquired from a patient and applied to the patient-specific model to determine an indication of a cardiac stroke volume and to provide an indication of a cardiac status.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 9A illustrates generally an example of an impedance waveform feature data set.

FIG. 9B illustrates generally an example of clinical test data.

FID. 9D illustrates generally an example of a correlation between actual cardiac output and an indication of cardiac output provided using a patient-specific model.

DETAILED DESCRIPTION

Figure 1:
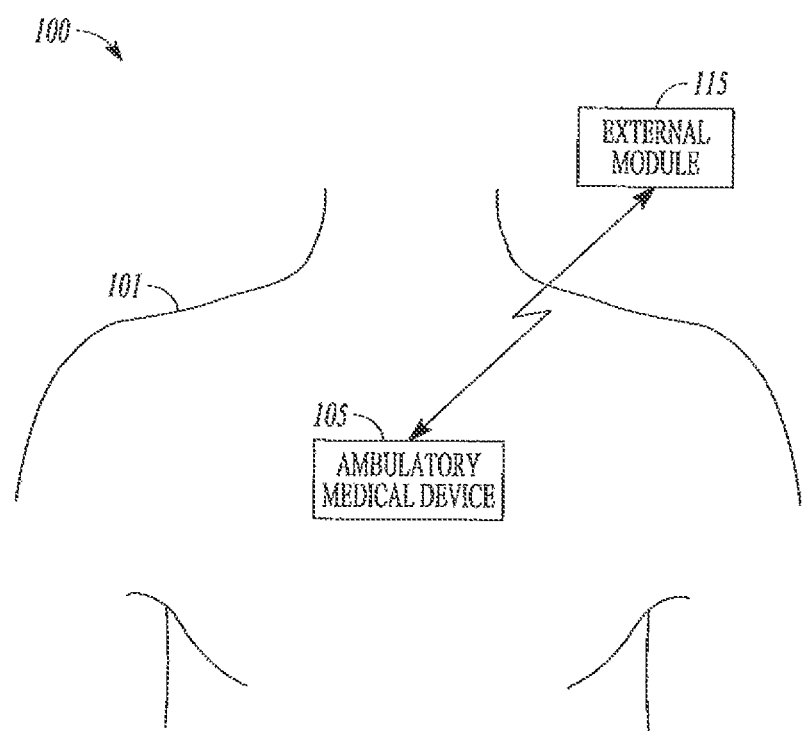
FIG. 1 illustrates generally an example that can include an ambulatory medical device and an external module.

FIG. 1 illustrates generally an example of a system 100 including an ambulatory or implantable medical device (IMD) 105 in a subject body 101, the IMD 105 wirelessly coupled to an external module 115. In an example, the IMD 105 can include one or more of a cardiac stimulating circuit, a cardiac sensing circuit, or a processor circuit. In certain examples, a functional portion of one or more of the cardiac stimulating circuit, cardiac sensing circuit, or the processor circuit can occur in the IMD 105, and another portion elsewhere (e.g., in an external programmer or analyzer circuit);

In an example, the IMD 105 can include a cardiac rhythm management device, such as a pacemaker, or a defibrillator, among other implantable medical devices. In an example, the IMD 105 can include an antenna configured to provide radio-frequency or other communication between the IMD 105 and the external module 115, or other external device.

In an example, the external module 115 can include an antenna. In an example, the external module 115 can include a local medical device programmer or other local external module, such as within wireless communication range of the IMD 105 antenna. The external module 115 can include a remote medical device programmer or one or more other remote external modules (e.g., outside of wireless communication range of the IMD 105 antenna, but coupled to the IMD 105 using a local external device, such as a repeater or network access point). The external module 115 can include a processor circuit configured to process information that can be sent to or received from the IMD 105. The information can include medical device programming information, subject data, device data, or other instructions, alerts, or other information. In an example, the external module 115 can be configured to display information (e.g., received information) to a user. Further, the local programmer or the remote programmer can be configured to communicate the sent or received information to a user or physician, such as by sending an alert via email of the status of the subject 101 or the system 100 components.

Figure 2:
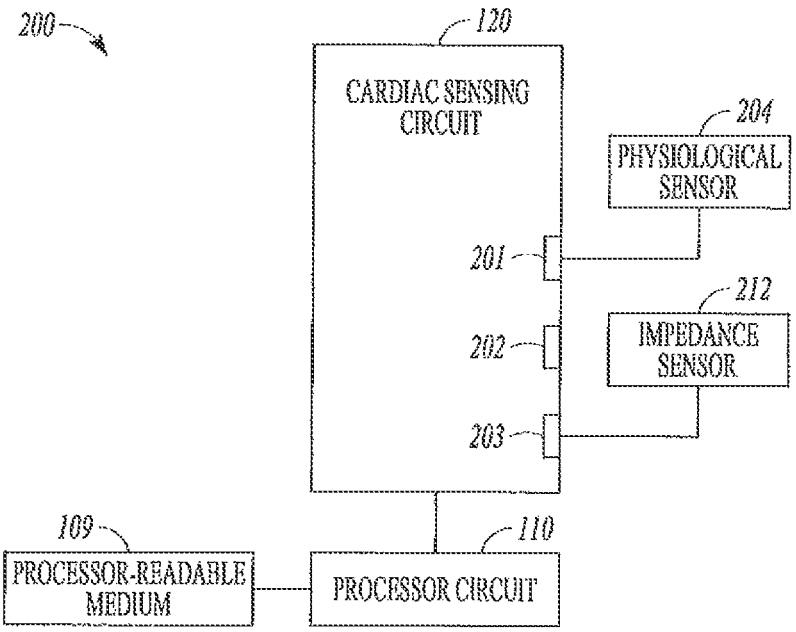
FIG. 2 illustrates generally an example that can include a processor circuit, a processor-readable medium, and a cardiac sensing circuit.

FIG. 2 illustrates generally an example of a system 200 that can include a processor circuit 110, a processor-readable medium 109, and a cardiac sensing circuit 120. In an example, the processor circuit 110 can be configured to access the processor-readable medium 109, such as to retrieve instructions that eau be used by the processor circuit 110 to control the cardiac sensing circuit 120. In an example, the processor circuit 110 can include one or more outputs, such as to provide information to the processor-readable medium 109 or to provide information to a communication circuit, such as can be communicatively coupled with the external module 115. The processor circuit 110 can include one or more inputs, such as can be configured to receive information from the cardiac sensing circuit 120 or the processor-readable medium 109, among other sources.

In an example, the cardiac sensing circuit 120 can include a first data input 201, a second data input 202, and a third data input 203. The system 200 can include a physiological sensor 204, such as can be communicatively coupled to the first data input 201. In an example, the system 200 can include an impedance sensor 212, such as can be coupled to the third data input 203.

In an example, the cardiac sensing circuit 120 can be configured to receive electrical information from in or near the heart and lungs, for example, over at least a portion of a cardiac or respiratory cycle, such as using one or more of the physiological sensor 204 or the impedance sensor 212, among other sensors. In an example, the electrical information can include an impedance waveform, an electrical cardiogram (ECG) signal (e.g., an evoked response, a subcutaneous ECG, or other), an electrical signal from a heart sound sensor such as a microphone, an electrical signal from an accelerometer configured to provide an indication of mechanical cardiac activity, an electrical signal from a pressure sensor configured to provide an indication of a pressure, such as a central venous pressure (CVP) or a right ventricle pressure, or one or more other electrical signals indicative of cardiac information.

The processor circuit 110 can be configured to determine a characteristic of information received from the cardiac sensing circuit 120. For example, the processor circuit 110 can be configured to extract one or more waveform features from impedance waveform information received using the impedance sensor 212 and the third data input 203. The impedance waveform information can be received from in or near the heart over at least a portion of the cardiac cycle, or over multiple cardiac cycles. In an example, the waveform features can include, among other features derivable from impedance waveform information, at least one of:

(1) a heart rate discerned from the impedance waveform information;

(2) an amplitude of a portion of the impedance waveform information;

(3) an integral of a portion of the impedance waveform information;

(4) a mean amplitude of a portion of the impedance waveform information;

(5) a maximum or minimum derivative of a portion of the impedance waveform information;

(6) a ratio of features derived from the impedance waveform information;

(7) a linear combination of waveform features derived front the impedance waveform information; or (8) a product of waveform features derived from the impedance waveform information.

The processor circuit 110 can be configured to collect a comprehensive list of several waveform features, and then select a sub-set from among the comprehensive list.

In an example, the processor circuit 110 can be configured to determine a characteristic of information received from the cardiac sensing circuit 120, such as information received from the physiological sensor 204 via the first data input 201. For example, the processor circuit 110 can be configured to analyze electrical information received from the physiological sensor 204 to obtain an indication of a cardiac stroke volume or cardiac output, such as a surrogate indication of a cardiac stroke volume. The indication of a cardiac stroke volume can be proportional to actual cardiac stroke volume or cardiac output, and need not be an actual measure of cardiac stroke volume or cardiac output. The surrogate indication of a cardiac stroke volume can include information that is related to a cardiac stroke volume, or information that can be used to derive a true stroke volume, among other types of information. In an example, the physiological sensor 204 can include, among other sensors, a heart rate sensor, a heart sound detector (e.g., a microphone or accelerometer), a respiration sensor (e.g., an impedance sensor, such as can receive information indicative of a respiration status), or a physical activity level sensor (e.g., a multi-axis accelerometer, a Hall effect sensor, etc.). In an example, the cardiac sensing circuit 120 or the processor circuit 110 can filter the information received from the physiological sensor 204, such as to remove high or low frequency vibration information.

Figure 3:
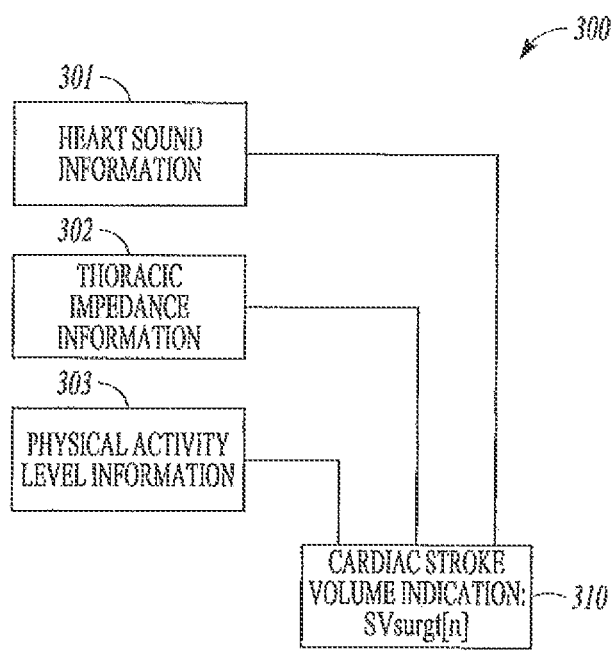
FIG. 3 illustrates generally an example that can include receiving an indication of a cardiac stroke volume.

FIG. 3 illustrates generally an indication of a cardiac stroke volume 310 (SVsurgt[n]) at a physical activity level n, and several kinds of information that can be used to determine SVsurgt[n]. For example, heart sound information 301 can provide SVsurgt[n] using systolic timing intervals, such as using the first and second heart sound timings with respect to the R-wave. This can be an especially useful measure at rest. In an example, heart sounds based ejection time (HSET), such as a time interval between the aortic components of S1 and S2, can be correlated with stroke volume as described by Patangay et. al. in "Heart Sounds Based Measures of Cardiac Status for Heart Failure Patient Management," IEEE EMBS Conference, 2009, at 3016.

In an example, thoracic impedance information 302, such as impedance-based minute ventilation information, can provide SVsurgt[n] as an indication of metabolic demand. In an example, a minute ventilation sensor can include a pair of current source electrodes and a pair of voltage sense electrodes.

In an example, physical activity level information 303 can be an indirect indicator of metabolic demand that can provide SVsurgt[n]. In an example, the cardiac sensing circuit 120 can receive information concurrently from the data inputs 201-203, such as to receive information from the impedance sensor 212 and physical activity level information indicative of SVsurgt[n] from a sensor (e.g., the physiological sensor 204).

The surrogate indication of cardiac stroke volume, SVsurgt[n], and impedance waveform features can be used to determine a model for cardiac stroke volume. In an example, the processor circuit 110 can be used to determine the model for cardiac stroke volume, or the model can be determined in a separate processor circuit, such as can be included in the external module 115. Methods and examples describing the derivation of the model are described at length below, such as in the discussion of FIG. 7 and FIG. 8. The model for cardiac stroke volume can be applied to patient information (e.g., information retrieved after the model is derived, such as using the cardiac sensing circuit 120) in a predictive sense, such as to provide an indication of a cardiac status. For example, waveform features derived from a test impedance signal can be applied to the model to determine a test indication of a cardiac stroke volume. In an example, the test indication of a cardiac stroke volume can be compared to a baseline cardiac stroke volume, or trended, such as to provide the indication of a cardiac status.

In an example, the indication of a cardiac status can include an indication of a likelihood of cardiac decompensation, such as in a heart failure patient. For example, a decrease in stroke volume over time, or a stroke volume that is lower than a threshold stroke volume, can be predictive of a decompensation event. In an example, the indication of a cardiac status can include an indication of cardiac remodeling. For example, in a patient receiving cardiac resynchronization therapy, the cardiac status can include information about how well that therapy is progressing. Cardiac remodeling can indicate an improvement in patient cardiac function, or can be used to indicate that a patient is a candidate for a cardiac resynchronization therapy (CRT) device. In another example, the indication of a cardiac status can include an indication of a severity of a ventricular arrhythmia, such as can be used to differentiate a sinus tachycardia from a potentially lethal ventricular tachycardia arrhythmia.

In an example, the processor circuit 110 can be configured to report (or make available) one or more indications of a cardiac status to an external device (e.g., the external module 115, an external programmer, directly to a clinician's handheld mobile device, email, etc.). In an example, the processor circuit 110 can be configured to provide an indication of a cardiac status for a plurality of cardiac cycles or physical activity levels. The processor circuit 110 can count, trend, or store one or more of the indications of a cardiac status, such as in a histogram, and, when SVsurgt[n] is at or near a defined threshold, the processor circuit 110 can be configured to do, among other things, one or more of the following:

(1) provide an alert to an external module;
(2) inhibit delivery of unnecessary stimulation energy;
(3) delay delivery of stimulation energy to treat an arrhythmia;
(4) provide an indication for CRT in patients with internal cardiac defibrillators; or
(5) predict acute decompensation in stable heart failure patients.

Figure 4:
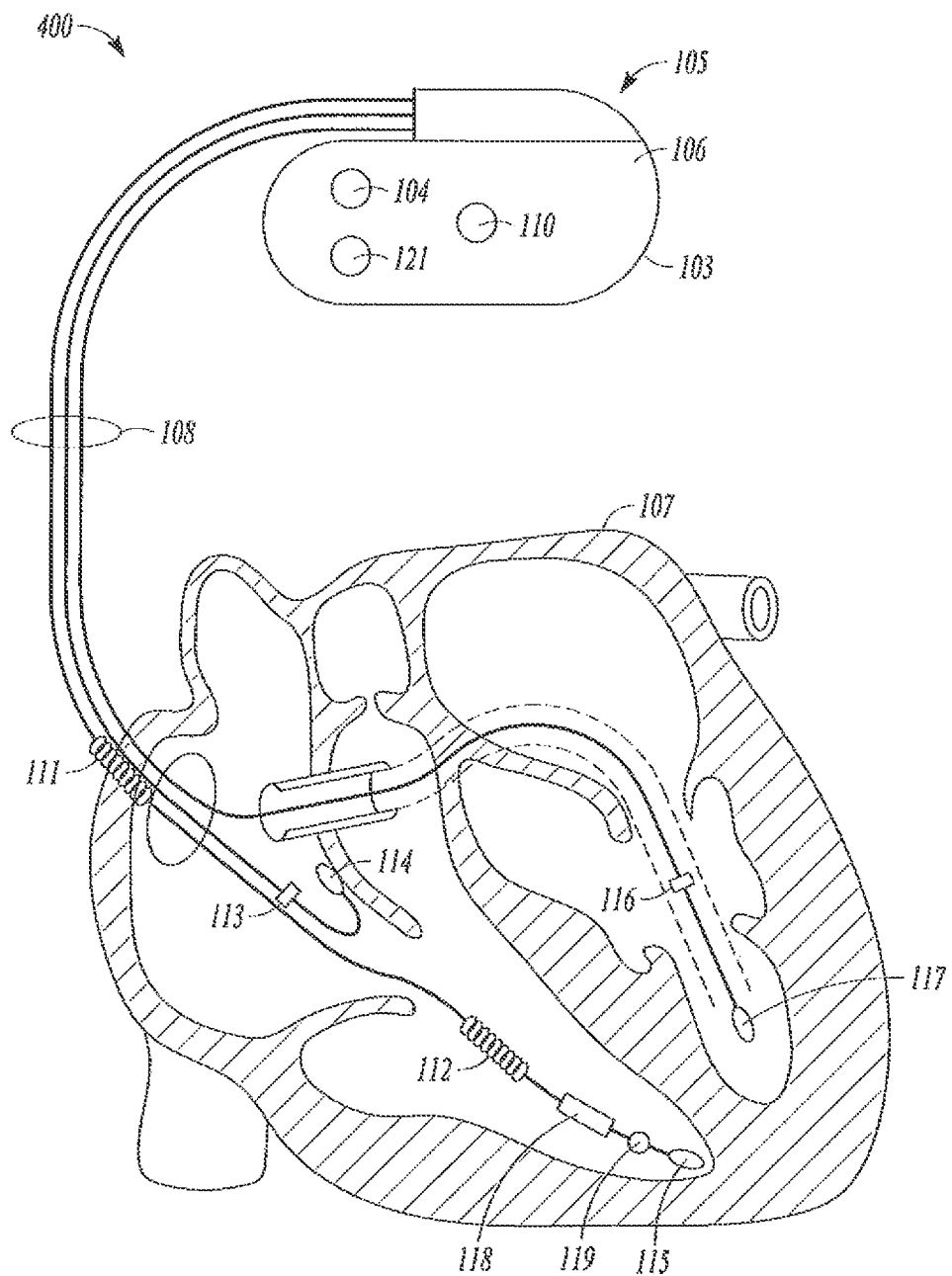
FIG. 4 illustrates generally an example that can include an implantable medical device and an implantable lead system, including leads disposed in a heart.

FIG. 4 illustrates generally an example of a system 400 that can include the IMD 105. In an example, the IMD 105 can include an implantable electronics unit 106. In an example, the electronics unit 106 can be electrically and physically coupled to an implantable lead system 108.

Portions of the implantable lead system 108 can be inserted into a patient's thorax, including into a patient's heart 107. The implantable lead system 108 can include one or more electrodes that can be configured to sense electrical cardiac activity of the heart, to deliver electrical stimulation to the heart, or to sense the patient's thoracic impedance. In an example, the implantable lead system 108 can include one or more sensors configured to sense one or more physiological parameters such as cardiac chamber pressure or temperature. Conductive portions of the housing 103 (or attached header) of the electronics unit 106 of the IMD 105 can optionally serve as an electrode, such as a "can" electrode.

A communications circuit can be included within the housing 103 (or attached header), such as to facilitate communication between the electronics unit 106 and the external module 115. The communications circuit can facilitate unidirectional or bidirectional communication with one or more implanted, ambulatory, external, cutaneous, or subcutaneous physiologic or non-physiologic sensors, patient-input devices, or information systems.

The IMD 105 can include a motion detector 104 that can be used to sense patient physical activity or one or more respiratory or cardiac related conditions, such as using the physiological sensor 204. In an example, the motion detector 104 can be configured to sense a physical activity level or chest wall movements associated with respiratory effort. In an example, the motion detector 104 can include a single-axis or multiple-axis (e.g., three-axis) accelerometer that can be located in or on the housing 103. An accelerometer can be used to provide information about patient posture, respiratory information including, for example, about rales or coughing, cardiac information including, for example, S1-S4 heart sounds, murmurs, or other acoustic information.

The processor circuit 110 can be included, such as within the housing 103. Systems and methods describing the acquisition of impedance-related information are further described in Belalcazar, U.S. Pat. No. 7,640,056, entitled "MONITORING FLUID IN A SUBJECT USING AN ELECTRODE CONFIGURATION PROVIDING NEGATIVE SENSITIVITY REGIONS," which is hereby incorporated by reference.

A storage circuit can be included, such as within the housing 103, for storing a plurality of values, including data trend information. In an example, values of surrogate indications of cardiac stroke volume can be stored in the storage circuit. In an example, the storage circuit can include a histogram-based storage mechanism to facilitate storage of quantitative attributes over an extended period. In an example, the storage circuit can be external to the IMD 105, or can be communicatively coupled to the IMD 105 via the communications circuit.

The implantable lead system 108 and the electronics unit 106 of the IMD 105 can incorporate one or more thoracic impedance or like signal sensors that can be used, for example, to acquire information about a patient's respiratory waveform or other respiration-related information. Illustrative examples of systems that can detect respiration signals and measure breathing volume are described in Hatlestad et al., U.S. Pat. No. 7,603,170 entitled "CALIBRATION OF IMPEDANCE MONITORING OF RESPIRATORY VOLUMES USING THORACIC D.C. IMPEDANCE," which is hereby incorporated by reference.

In an example, a thoracic impedance signal sensor can include, for example, one or more intracardiac electrodes 111-118, such as can be positioned in one or more chambers of the heart 107. The intracardiac electrodes 111-118 can be coupled to an impedance drive/sense circuit 121, such as can be positioned within the housing 103 of the electronics unit 106.

In an example, the impedance drive/sense circuit 121 can be configured to generate a current that flows through the tissue, such as between an impedance drive electrode 113 and a Can electrode on the housing 103 of the electronics unit 106. The voltage at an impedance sense electrode 114 relative to the Can electrode can change as the patient's thoracic impedance changes. The voltage signal developed between the impedance sense electrode 114 and the Can electrode can be detected by the impedance drive/sense circuit 121. Locations or combinations of impedance sense or drive electrodes other than those illustrated in FIG. 4 are possible.

The implantable lead system 108 can include one or more cardiac pace/sense electrodes 113-117, such as can be positioned in, on, or about one or more heart chambers such as for sensing one or more electrical signals from the patient's heart 107. The intracardiac sensing and pacing electrodes 113-117, such as those shown in FIG. 4, can be used to sense or pace one or more chambers of the heart, such as the left ventricle (LV), the right ventricle (RV), the left atrium (LA), or the right atrium (RA). The implantable lead system 108 can include one or more defibrillation electrodes (e.g., electrodes 111 and 112), such as for delivering defibrillation or cardioversion shocks to the heart 107 or for sensing one or more intrinsic electrical signals from the heart 107.

In an example, the implantable lead system 108 can include one or more other physiological sensors. For example, the lead system 108 can include a pressure sensor 119, such as can be disposed on an endocardial lead to monitor hemodynamic changes, such as a variation in pressure within a right ventricle of the heart 107. In an example, the pressure sensor 119 can be a transducer, including a piezo-resistive element mounted on a silicon diaphragm behind a compliant membrane window.

Figure 5:
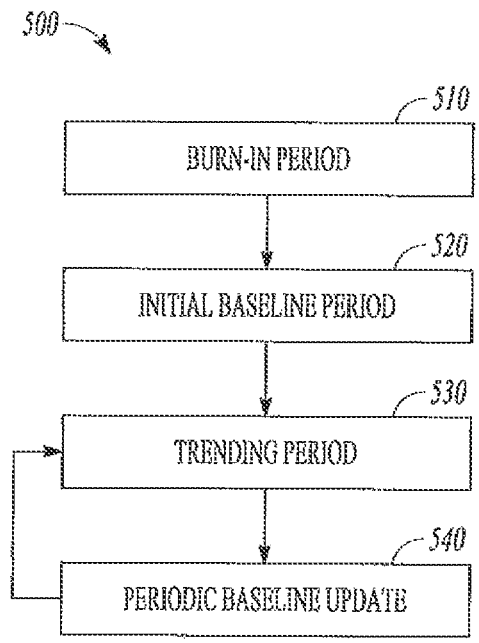
FIG. 5 illustrates generally an example that can include a burn-in period, an initial baseline period, a trending period, and a periodic baseline update.

FIG. 5 illustrates generally several operating states 500 of the present invention. The operating states can include a burn-in period 510, an initial baseline period 520, a trending period 530, and a periodic baseline update 540.

The burn-in period 510 can begin any time, such immediately after implant of the IMD 105, and can continue for several weeks or until inflammation of thoracic tissue subsides and lead impedances, such as can be measured using the implantable lead system 108, are sufficiently stable.

The initial baseline period 520 can follow the burn-in period 510. The initial baseline period 520 can include receiving physiological information, such as using the cardiac sensing circuit 120. In an example, the physiological information can be averaged, such as over a period of multiple days, using the processor circuit 110. The physiological information can include reference impedance information, such as can be received using the implantable lead system 108. In an example, the reference impedance information can include reference waveform features derived from a reference impedance waveform, such as can be received using an array of electrodes disposed in or near the heart 107. The reference waveform features can include, among others attributes, a peak-to-peak amplitude, a mean amplitude, a difference amplitude, or an integral of a portion of the reference impedance waveform, as described above in the discussion of FIG. 2. In an example, the reference waveform features can be derived from a reference impedance waveform obtained using a 20 hertz sampling rate. In other examples, a higher sampling rate can be used, such as to receive more robust waveform features based on a integral or derivative of a portion of the reference impedance waveform.

Reference impedance information or waveforms can be collected using several impedance vectors. For example, a first vector can include an RV-Can vector, such as between a distal tip electrode disposed in a right ventricle, and a can electrode integrated into the IMD 105. A second vector can include a bipolar vector, such as between a distal tip electrode 115 and a ring electrode 118, such as can be disposed on one lead disposed in the heart 107. In an example, the reference impedance information can be collected concurrently from multiple vectors, or the reference impedance information can be collected sequentially from multiple vectors. In an example, reference impedance information can be collected at a first vector for a first duration (e.g., 30 seconds), and additional reference impedance information can be collected at a second vector for a subsequent duration (e.g., 30 seconds). In an example, the duration can be selected to minimize variability due to periodic motion, such as due to breathing or due to a heartbeat. For example, at a standard breathing rate of 12-16 breaths per minute, impedance information can be received for about 15 seconds, or 3-4 breaths, such that the average of the impedance information can be used to minimize the effect on impedance due to breathing.

In an example, the initial baseline period 520 can include receiving physiological information using the physiological sensor 204. The physiological information can include, among other things, an intracardiac pressure, such as obtained using the pressure sensor 119, or a physical activity level that can be obtained using the motion detector 104.

The initial baseline period 520 can include establishing a baseline surrrogate indication of a cardiac stroke volume at a first physical activity level, SVsurgt[1]. In an example, SVsurgt[1] can be obtained using the physiological sensor 204. SVsurgt[1] can be used, such as in combination with reference waveform features, to establish a model for determining an indication of patient cardiac stroke volume. The model can be applied to waveform features derived from test impedance information to determine an indication of a patient cardiac stroke volume. In an example, the model can be a linear combination of extracted reference waveform features and constants, such as:

$$SVsurgt[1] = K1*F1 + K2*F2 + K3*F3 + K4 + K5*HR \quad (1)$$

where F1 is a first reference waveform feature, F2 is a second waveform feature, F3 is a third waveform feature, HR is heart rate, and K1, K2, K3, K4, and K5 are constants.

The selection of the type and number of reference waveform features, and thus the determination of the constants (e.g., K1-K5), can be unique for each patient. For example, see the discussion of FIG. 8, below. The uniqueness of the constants can be due to several factors including lead position, lead-tissue contact quality, heart morphology, and differences in blood or tissue resistivity, among others. New or additional reference waveform features or constants can be configured as needed, such as during a periodic baseline update 540.

In an example, a model can be derived using information extracted from one or more physiological signals, wherein the physiological signals can be obtained at several different physical activity levels, or within several ranges of physical activity. In an example, multiple different models can be calculated for each of several physical activity levels, or several ranges of physical activity, such as a model directed at relatively low levels of physical activity, and a different second model directed at relatively vigorous levels of physical activity.

A physical activity level can include a range of physical activity levels that can be associated with one another. In an example, a first model and corresponding model coefficients can be calculated using SVsurgt[1], received at a first physical activity level, and reference impedance information received at the same first physical activity level. A second model can be calculated using SVsurgt[2] received at a second physical activity level, and reference impedance information received at the same second physical activity level. Data can be collected and models can be derived over a range of activity levels (e.g., including at rest, at moderate physical activity, or at a strenuous level of physical activity). By collecting information including indications of a cardiac stroke volume and impedance information over a range of activity levels, several models can be determined. In an example, the range of physical activity levels can overlap, and need not be at the extremes of possible physical activity.

Test impedance information, such as can be acquired near to but outside of any of the ranges of physical activity for which models are available, can be applied to an extrapolated model. For example, data received during the initial baseline period 520 can correspond to normal, or non-pathological, stroke volume levels, such as can be obtained over a first range of physical activity levels. In an example, the first range can include a resting physical activity level and at least one more strenuous physical activity level. The model derived during the initial baseline period 520 can accurately predict stroke volume at least within this first range of physical activity. In an example, a pathological, lower stroke volume level can be used to predict decompensation. This level can be outside of the range used during the initial baseline period 520. The value of the stroke volume in this case can be extrapolated from a set of predictors, such as using a linear extrapolation technique. In an example; when extrapolating to a value lower than the model range (e.g., outside of the first range of physical activity levels), the values of several extracted waveform features can tend toward zero. For example, a magnitude of a peak-to-peak impedance can tend toward zero as the stroke volume decreases toward zero. In an example where the data require extrapolation outside of an optimal model region (e.g., outside of the first range of physical activity levels), the model may not predict stroke volume as accurately as within the optimal model region. However, the relative indication of the cardiac stroke volume can still be useful to indicate that cardiac decompensation is occurring or impending.

In the example of equation (1), at least five measurements, corresponding to five different physical activity levels, can be required to determine the five constants, K1, K2, K3, K4, and K5, assuming a linear model. The number of required measurements can be reduced by reducing the number of waveform features included in the model; however, the accuracy of the model can be affected by reducing the number of waveform features in the model. For example, if the model is:

$$SV\text{surgt}[n]=C1*F1+C2*F2+C3+C4*HR \qquad (2)$$

then only four measurements are required to uniquely determine the four constants, C1, C2, C3, and C4. A goodness-of-fit between the model and an actual measure of stroke volume or cardiac output (e.g., an $r^2$ value, or an adjusted $r^2$ value) of the four-constant model may be adversely affected by the decrease in model parameters. In some examples with carefully selected waveform features, a four-constant (or fewer) model can be sufficient for diagnostic purposes. An $r^2$ value and its relation to the number of waveform features is further discussed below at FIG. 9.

In the example of FIG. 5, a trending period 530 can follow the initial baseline period 520. The trending period 530 can include acquiring test impedance data, such as using the cardiac sensing circuit 120. In an example, the trending period 530 can include computing a test indication of a cardiac stroke volume, SVtest[n], such as using the test impedance data and a model established during the initial baseline period 520 corresponding to the patient physical activity level, n, at the time the test impedance data was acquired.

Periodic comparisons, such as daily comparisons, of SVtest[n] to SVsurgt[n] can provide cardiac status diagnostic information. Similarly, storing and trending patient cardiac stroke volume information can be used to provide cardiac status diagnostic information. For example, as SVtest[n] is trended over a period of several days, an overall decrease in SVtest[n] can be predictive of a cardiac decompensation event.

At 540, a periodic baseline update can follow a period of SVtest[n] trending, such as to improve the efficacy of diagnostic information obtained from the models. For example, cardiac remodeling can require establishing a new baseline surrogate indication of a cardiac stroke volume and corresponding impedance information and coefficients (e.g., the coefficients K1-K5, or C1-C4).

In an example, the periodic baseline update 540 can include receiving additional physiological information, such as physical activity level information and impedance information, such as over one or more ranges of physical activity. In an example, the received additional physiological information can be reference impedance information, such as described above in the discussion of the initial baseline period 520. The reference impedance information can be updated to reflect changes in tissue physiology or to accommodate a physical displacement of electrode leads (e.g., one or more of the leads in the implantable lead system 108) disposed in or near the heart 107, among other reasons. In an example, the reference impedance information can be periodically updated to reflect other changes in patient physiology, such as cardiac remodeling, or to accommodate a new or intermediate physical activity level. The periodic baseline update 540 can include receiving additional or updated surrogate indications of a cardiac stroke volume, such as at a first activity level, SVsurgt[1], or over a range of several activity levels. New models can be established using the received additional physiological information, including deriving new coefficients (e.g., the coefficients K1-K5).

The periodic baseline update 540 can be triggered automatically, such as after the processor circuit 110 determines a substantial deviation in a normal daily impedance, or on a periodic basis, such as once each week. In an example, a baseline update can occur at a time when it can be verified that the patient is not in heart failure. A trending period 530 can follow a periodic baseline update 540, such as to identify a cardiac status.

Figure 6:
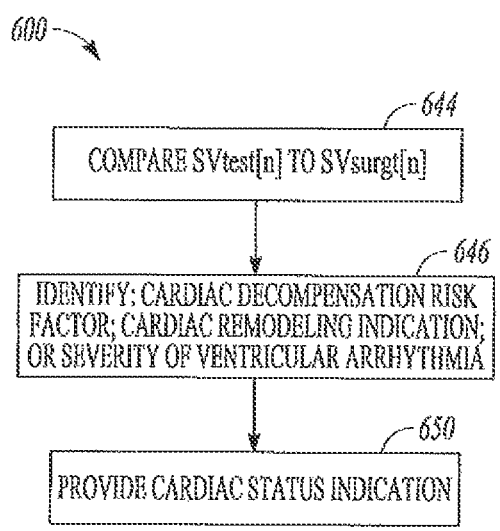
FIG. 6 illustrates generally an example that can include comparing cardiac stroke volumes, identifying a cardiac status, and providing an indication of a cardiac status.

FIG. 6 illustrates generally a method that can include comparing SVtest[n] to SVsurgt[n] 644, identifying a cardiac status 646, and providing a cardiac status indication 650. In an example, SVsurgt[n] can be determined at rest (e.g., during sleep, or at the same time each day). SVtest[n] can be determined at the same time of day, such as on a subsequent day, or at the same time over a series of subsequent days. At 644, SVtest[n] can be compared to SVsurgt[n]. At 646, a cardiac status can be identified using the comparison at 644. For example, if SVtest[n] is less than SVsurgt[n] by a predetermined percentage (e.g., 20%) in a normal ICD patient, an increased risk of heart failure can be identified, such as a cardiac decompensation risk factor. At 650, the processor circuit 110 can be configured to provide the cardiac status indication, such as by alerting a care provider or patient of the cardiac decompensation risk factor. In an example, another cardiac status can be identified at 646. For example, if SVtest[n] is more than SVsurgt[n] by a predetermined percentage (e.g., 10%) in a stable CRT patient, the processor circuit 110 can be configured to alert a care provider of beneficial cardiac remodeling, such as at 650.

At 646, additional cardiac status information can be identified. For example, a substantive decrease in SVtest[n] compared to a baseline indication of a cardiac stroke volume can be indicative of a lethal arrhythmia and can indicate a reason to provide a stimulation energy to the heart. In an example, providing the cardiac status indication at 650 can include providing instructions to the processor circuit 110 to provide or inhibit cardiac stimulation energy. Stimulation energies can be indicated for other reasons, such as rapid heart rate. Stimulation energies can also be delayed, for example, if SVtest[n] is stable while other anti-tachyarrhythmia pacing schemes are attempted. In an example, using SVtest[n] during a tachyarrhythmia event can require an increased sampling rate of the test impedance information (e.g., more than 20 hertz), and may require less or no averaging (i.e., impedance data can be acquired for less than 15 seconds). In an example, the data acquisition trigger could be the start of the tachyarrhythmia event instead of a fixed time of day.

Figure 7:
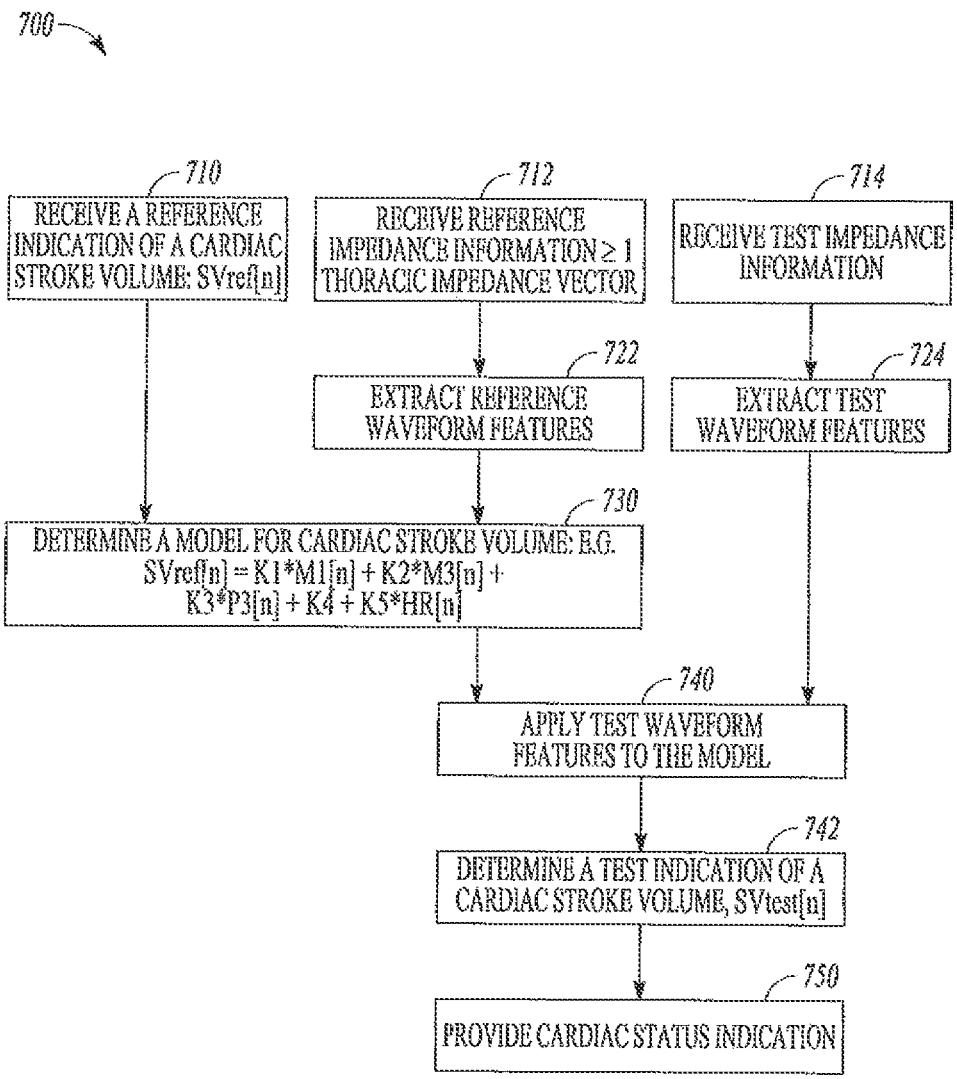
FIG. 7 illustrates generally a graphical representation of a method that can be used to provide a cardiac status indication using a patient-specific model.

FIG. 7 illustrates generally an example that can include receiving reference information, receiving test information, extracting waveform features, and using the features to provide a cardiac status indication.

In the example of FIG. 7, a reference indication of a cardiac stroke volume, SVref[n], can be received at 710, where n corresponds to a discrete physical activity level or physical activity level range. SVref[n] can be received such as according to the discussion of SVsurgt[n] at FIG. 3. For example, heart sound information 301 can be used to provide the reference indication of a cardiac stroke volume, SVref[n]. At 712, reference impedance information can be received, such as using a first thoracic impedance vector (e.g., an impedance vector associated with the right side of the heart), a second thoracic impedance vector (e.g., an impedance vector between a tip electrode disposed in the left ventricle and a can electrode, such as on the IMD 105), or other thoracic impedance vector. The reference impedance information can include an impedance waveform signal. Waveform features can be extracted from the reference impedance information at 722, such as from the impedance waveform signal. The waveform features extracted at 722 can include signal amplitude information, average signal amplitude information, signal integral or derivative information, or a linear combination of signal information, among other features, and as described above. The waveform features can correspond to respective thoracic impedance vectors. For example, an amplitude feature can be extracted from a first vector, and a derivative feature can be extract from a second vector. In an example, the selection of the waveform features can be unique to each patient, such as to account for differences in patient physiology or differences in electrode lead placement between patients, among other reasons.

At 730, a model for cardiac stroke volume can be determined. In an example, the model for cardiac stroke volume can be of the form:

$$SVref[n]=K1*M1[n]+K2*M3[n]+K3*P3[n]+K4+K5*HR[n] \quad (3)$$

where n corresponds to a physical activity level or physical activity level range. K1, K2, K3, K4, and K5 can represent constants. The elements operated on by the constants can include M1[n], M3[n], P3 [n], or HR[n], among others, wherein these elements can represent one or more waveform features or numerical values indicative of waveform features. For example, M1[n] can represent a mean of a waveform feature extracted from a first thoracic impedance vector at a physical activity level n. In an example, M1[n] can represent a mean of an impedance over one or more cardiac cycles, such as can be measured using a first thoracic impedance vector. M3[n] can represent a mean of an impedance over one or more cardiac cycles, such as can be measured using a third thoracic impedance vector at the physical activity level n. P3 [n] can represent a peak-to-peak amplitude of an impedance over one or more cardiac cycles, such as can be measured using the third thoracic impedance vector at the physical activity level n. HR[n] can represent a heart rate at the activity level n.

In an example, patient data can be collected over five patient physical activity levels (i.e., n=1, 2, 3, 4, 5), such as during an initial baseline period 520, and the data can be analyzed to determine the five constants, K1-K5. The five activity levels can be non-overlapping, discrete intervals of physical activity. For example, a first indication of a cardiac stroke volume, such as corresponding to a first physical activity level, such as a resting physical activity level during sleep, SVref[1], can be determined according to:

$$SVref[1]=K1*M1+K2*M3[1]+K3*P3[1]+K4+K5*HR[1].$$

Similarly, a second indication of a cardiac stroke volume, such as corresponding to a second physical activity level, such as a resting physical activity level not during sleep, SVref[2], can be determined according to:

$$SVref[2]=K1*M1[2]+K2*M3[2]+K3*P3[2]+K4+K5*HR[2].$$

Additional indications of a cardiac stroke volume, corresponding to several additional, different physical activity levels, can be determined according to:

$$SVref[3]=K1*M1[3]+K2*M3[3]+K3*P3[3]+K4+K5*HR[3];$$

$$SVref[4]=K1*M1[4]+K2*M3[4]+K3*P3[4]+K4+K5*HR[4]; \text{ and}$$

$$SVref[5]=K1*M1[5]+K2*M3[5]+K3*P3[5]+K4+K5*HR[5].$$

Taken together, this system of five equations can be used to determine the five constants, K1-K5, such as using a linear combination method, a graphical method, a matrix method, a substitution method, or an elimination method, among other techniques.

At 730, the model for cardiac stroke volume can be determined using any number of waveform feature variables and constants. As few as one waveform feature can be used to determine the model, or as many waveform features as is practicable under the limitations of the implementing system (e.g., processor capability, power consumption, and data storage capacity can be limiting considerations). For example, a model for cardiac stroke volume can be, among others, any of:

$$SVref[n]=K1*M4[n]+K2 \quad (4)$$

$$SVref[n]=K1*P2[n]+K2*P3[n]+K3 \quad (5)$$

$$SVref[n]=K1*M2[n]K2*HR[n]+K3 \quad (6)$$

The model for cardiac stroke volume can be selected in several ways. For example, the model can be determined after a technician carefully analyzes data from the available thoracic impedance vectors and physiological sensors to find the model that serves as a best predictor (e.g., an adjusted $r^2$ value representing test and actual stroke volume is optimized; see FIG. 9D). In an example, the model can be automatically selected, such as using a device programmer with a model-selection algorithm. For example, the algorithm could include forming multiple models and testing each model using $r^2$ values, adjusted $r^2$ values, or other metrics. Available models can be limited by the number of different thoracic impedance vectors and physiological sensors that are available to the processor circuit 110, and the system capacity to process models with many variables.

At 714, test impedance information can be received, such as using the same thoracic impedance vectors used to receive the reference impedance information at 712. At 724, test waveform features can be extracted using the test impedance information. In an example, the test impedance information received at 714 can include information from a first thoracic impedance vector (e.g., an impedance vector associated with the right side of the heart), or a second thoracic impedance vector (e.g., an impedance vector between a tip electrode disposed in the left ventricle and a can electrode, such as on the IMD 105), among others. Waveform features can be extracted from the test impedance information at 724. In an example, the test impedance information can include an impedance waveform signal. The test waveform features extracted at 724 can include the same kind of waveform features extracted from the reference impedance information at 722. For example, the test waveform features can include signal amplitude information, average signal amplitude information, signal integral or derivative information, or a linear combination of signal information, among other features. The waveform features can correspond to respective thoracic impedance vectors. For example, if a first waveform feature is a peak-to-peak amplitude of an impedance signal of an RV-Can vector, the peak-to-peak amplitude of the RV-Can vector can be determined for each of the reference impedance information and the test impedance information.

At 740, the test waveform features (e.g., extracted at 724) can be applied to the model for cardiac stroke volume (e.g., the model determined at 730). In the example of equation (3), M1[n] can indicate a mean of reference waveform features received from a first thoracic impedance vector at an activity level n (e.g., a mean of an impedance amplitude measured over a predetermined number of cardiac cycles) for the purpose of determining the model for cardiac stroke volume. In applying the model at 740, M1[n] can indicate a mean of test waveform features extracted from the same first thoracic impedance vector at the activity level n. Similarly, to determine the model for cardiac stroke volume, HR[n] can indicate heart rate information obtained at the activity level n, such as at or near the time the reference impedance information is acquired. In applying the model at 740, HR[n] can indicate heart rate information obtained at the activity level n, such as at or near the time the test impedance information is acquired.

At 742, a test indication of a cardiac stroke volume, SVtest[n], can be determined, wherein n refers to the physical activity level or physical activity level range, and M1[n], M3[n], and P3[n] can indicate test waveform features (e.g., extracted from the test impedance information at 724), and HR[n] can indicate heart rate at physical activity level n. In an example, SVtest[n] can include as few as one waveform feature, or as many waveform features as is practicable under system limitations. See equations 4, 5, and 6, for examples of other possible models for determining SVtest[n]. The number of available models can depend on the number of waveform features that are available.

At 750, a cardiac status indication can be provided, such as using SVtest[n] determined at 742. In an example, the cardiac status indication can be provided, such as using the method presented above in FIG. 6. For example, SVtest[n] can be compared to SVref[n], or SVtest[n] can be compared to a baseline stroke volume, or other threshold value. Where SVtest[n] shows an increase in stroke volume over SVref[n], cardiac remodeling can be indicated. A decrease in SVtest[n] compared to SVref[n] can indicate a serious condition, such as an increased risk of a cardiac decompensation episode in a heart failure patient. In an example, SVtest[n] can be trended over a period of a time, such as to provide the cardiac status indication.

Figure 8:
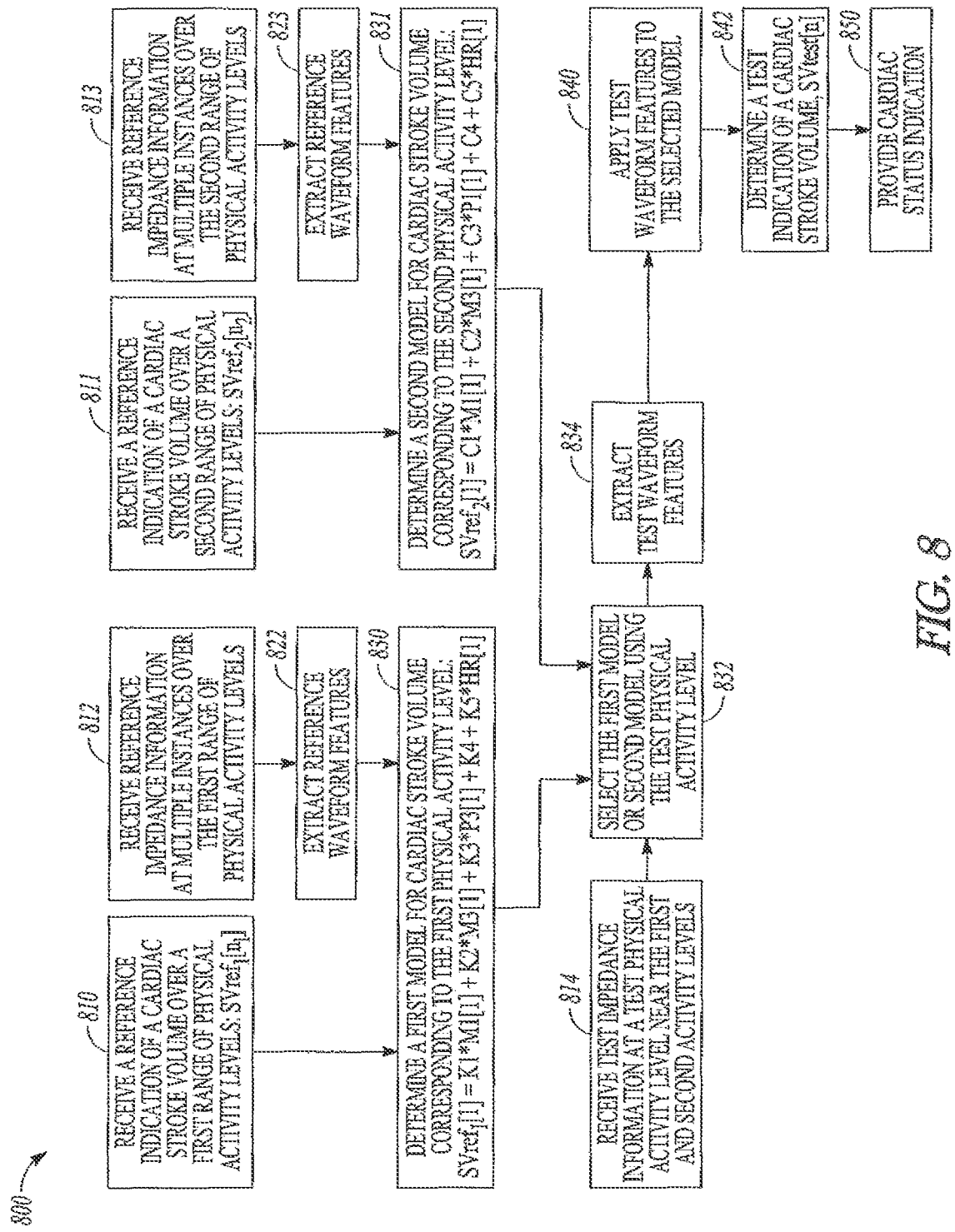
FIG. 8 illustrates generally a graphical representation of a method that can be used to provide a cardiac status indication using one of several patient-specific models.

FIG. 8 illustrates generally a method that can include receiving reference information at more than one activity level, receiving test information, and applying the test information to an appropriate model. For example, a reference indication of a cardiac stroke volume corresponding to a first range of physical activity levels can be received at 810, and a reference indication of a cardiac stroke volume corresponding to a second range of physical activity levels can be received at 811. In an example, the first and second ranges of physical activity levels can be non-overlapping ranges of physical activity levels.

Reference impedance information can be received at 812, such as at multiple instances over the first range of physical activity levels. For example, the reference impedance information can be collected continuously over a period of multiple patient breaths or cardiac cycles, or over a period of several seconds (e.g., 30 seconds). In an example, the reference impedance information can be collected at discrete intervals, such as every 50 milliseconds during a 30 second window. Similarly, additional reference impedance information can be received at 813, such as over a different, second range of physical activity levels.

In an example, receiving reference impedance information at 812 and 813 can include receiving reference impedance information from multiple thoracic impedance vectors. The reference impedance information can be received from the multiple vectors in parallel (e.g., concurrently, such as using parallel data inputs in the cardiac sensing circuit 120), or in series. For example, information from a first thoracic impedance vector can be received during a first time period (e.g., a 20 second period from t=0 to t=20 seconds), and information from a second thoracic impedance vector can be received during a second, subsequent time period (e.g., t=20 to t=40 seconds), wherein the first and second time periods correspond to approximately the same patient physical activity level.

Reference waveform features can be extracted from the reference impedance information received at 822 and 823. The waveform features can include any of the features described above, among other features.

In the example of FIG. 8, at 830, a first model for cardiac stroke volume, SVref$_1$[n], corresponding to the first range of physical activity levels, can be determined. For example, as discussed above at 730, patient data can be collected over at least five patient physical activity levels (i.e., n=1, 2, 3, 4, 5), such as during an initial baseline period 520, and the data can be analyzed to determine the five constants, K1-K5, such as using the equations:

$$SVref_1[1]=K1*M1[1]+K2*M3[1]+K3*P3[1]+K4+K5*HR[1];$$

$$SVref_1[2]=K1*M1[2]+K2*M3[2]+K3*P3[2]+K4+K5*HR[2];$$

$$SVref_1[3]=K1*M1[3]+K2*M3[3]+K3*P3[3]+K4+K5*HR[3];$$

$$SVref_1[4]=K1*M1[4]+K2*M3[4]+K3*P3[4]+K4+K5*HR[4]; \text{ and}$$

$$SVref_1[5]=K1*M1[5]+K2*M3[5]+K3*P3[5]+K4+K5*HR[5],$$

wherein each equation corresponds to a different physical activity level. As above, when this system of equations is analyzed together, the five constants K1-K5 can be determined using a suitable algebraic or other method of analysis.

At 831, a second model for cardiac stroke volume, SVref$_2$[n], corresponding to the second range of physical activity levels, can be determined, such as using the equations:

$$SVref_2[1]=C1*M1[1]+C2*M3[1]+C3*P1[1]+C4+C5*HR[1];$$

$$SVref_2[2]=C1*M1[2]+C2*M3[2]+C3*P1[2]+C4+C5*HR[2];$$

$$SVref_2[3]=C1*M1[3]+C2*M3[3]+C3*P1[3]+C4+C5*HR[3];$$

$$SVref_2[4]=C1*M1[4]+C2*M3[4]+C3*P1[4]+C4+C5*HR[4]; \text{ and}$$

$$SVref_2[5]=C1*M1[5]+C2*M3[5]+C3*P1[5]+C4+C5*HR[5].$$

In an example, the models SVref$_1$[n] and SVref$_2$[n] can use the same reference waveform features corresponding to their respective ranges of physical activity levels. For example, SVref$_1$[n] and SVref$_2$[n] can each include M1[n], a mean amplitude of the first impedance vector. In an example, the models SVref$_1$[n] and SVref$_2$[n] can use different reference waveform features. For example, SVref$_1$[n] can include M1[n], and SVref$_2$[n] can include a different reference waveform feature (e.g., M2[n]). In an example, SVref$_1$[n] can include P3[n], and SVref$_2$[n] can include P1[n].

In the example of FIG. 8, the models SVref$_1$[n] and SVref$_2$[n] use several of the same reference waveform features, including M1[n], M3[n], and HR[n]. Nonetheless, the values attributed to these reference waveform features will likely be unique because they refer to a unique patient physiology at a particular physical activity level. For example, M1[n] can be uniquely valued because the mean amplitude feature obtained from the fast vector at a first physical activity level within the first range of physical activity levels (i.e., M1[1]) can be different from the mean amplitude feature obtained from the first vector at a different, second physical activity level within the second range of physical activity levels.

Test impedance information can be received at 814. In an example, the test. impedance information can be received at a test physical activity level that is near the first and second ranges of physical activity levels (see, e.g., 810, 811, 812, 813). The first model for cardiac stroke volume, SVref$_1$[n], or the second model for cardiac stroke volume, SVref$_2$[n], can be selected at 832. In an example, the first model can be a better predictor over the first range of physical activity levels, such as near-resting physical activity levels. The second model can be a better predictor over the second range of physical activity levels, such as physical activity levels associated with strenuous exercise. In an example, information about a physical activity level can be determined using the test impedance information received at 814, such as using heart rate information derived from the impedance information. In an example, the test impedance information received at 814 can be near to but outside of the first and second ranges of physical activity levels.

In an example, the test physical activity level can be within one of the first or second ranges of physical activity levels. In an example where the test physical activity level is within the first range of physical activity levels, SVref$_1$[n] can be selected. In an example, the test physical activity level can be outside of the range of the first and second ranges of physical activity levels but near enough that the application of the models can be extrapolated. Similarly, the test physical activity level can be intermediate the first and second physical activity levels such that the application of the models can be interpolated. In an example, such as where the reference physical activity level ranges overlap or where a test physical activity is near multiple reference activity levels, more than one model can be selected.

In an example, test waveform features can be extracted at 834, such as using the test impedance information received at 814. The extracted waveform features can include a comprehensive collection of all available waveform features. Or, in a more efficient example, the extracted waveform features can be limited to those features present in the model selected at 832. In the example of FIG. 8, only the waveform features M1, M3, P3, and HR need to be extracted from the test impedance information received at 814.

At 840, the extracted test waveform features can be applied to the model selected at 832. At 842, a test indication of a cardiac stroke volume, SVtest[n], is determined by applying the test waveform features to the selected model at 840. At 850, an indication of a cardiac status can be provided, such as according to the discussion of FIG. 7 at 750, above.

FIG. 9A illustrates generally an example of a set of data that can be used to provide an indication of a cardiac status, such as according to FIG. 8 at 850. The chart 901 can include several columns, including Mean Physical Activity Level, Heart Rate, and, for each of multiple thoracic impedance vectors (e.g., Vector 1, Vector 2, and Vector 3), Ipeak-to-peak ($P_{[n]\text{-}Vector[y]}$), Imean ($M_{[n]\text{-}Vector[y]}$), and Ipeak-to-peak*Imean ($X_{[n]\text{-}Vector[y]}$), where n corresponds to a physical activity level, and y corresponds to a vector. "I" (as in Ipeak-to-peak, etc.) can indicate that these values are derived from an impedance signal.

The chart 901 can include several rows, such as can correspond to a subset of measurements acquired at a physical activity level, Range z (e.g., Range 1, Range 2, etc.). In an example, the first data row can correspond to a first physical activity level, such as a minimal patient physical activity level during sleep. The first data row can include heart rate information, and information about Ipeak-to-peak, Imean, and Ipeak-to-peak*Imean for each of three different thoracic impedance vectors at the first physical activity level (e.g. a resting physical activity level). For example, each of HR1, $P_{1\text{-}Vector1}$, $M_{1\text{-}Vector1}$, $X_{1\text{-}Vector1}$, etc., can represent numerical values. In an example, a model for cardiac stroke volume can be formed using the data set in the chart 901, such as:

$$SVsurgt[n]=K1*M1_{[n]\text{-}Vector[B]}+K2*M_{[n]\text{-}Vector[C]}+K3*P_{[n]\text{-}Vector[A]}+K4+K5*HR[n] \quad (7)$$

where n represents a physical activity range, and A, B, and C represent one of the vectors Vector 1, Vector 2, or Vector 3.

FIG. 9B illustrates generally an example of reference information, in a chart 902, from several test subjects. The reference information can be determined using reference impedance information (e.g., the reference impedance information received at 812). For example, using equation (7) as the model for cardiac stroke volume for Subject 4, the product of the constant K1 and Imean of Vector 2 (e.g., at a physical activity level n) is −5.52. Similarly, K3 multiplied by the average Ipeak-to-peak at the same physical activity level is −0.17. Using the reference information in the chart 902 and equation (7), an indication of a cardiac stroke volume can be calculated. If an indication of a cardiac stroke volume is already known, such as from the physiological sensor 204, equation (7) can be used to determine a value for each of the coefficients K1, K2, K3, K4, and K5. In an example, the form of the model (e.g., equation (7)), including the type and number of reference waveform features included in the model, can be the same for each subject (e.g., for each of the Subjects 1 through 8 in FIG. 9B). Although the form of the model can be the same, the coefficients K1, K2, K3, K4, and K5 can be uniquely valued for each subject.

Figures 9C, 9D:
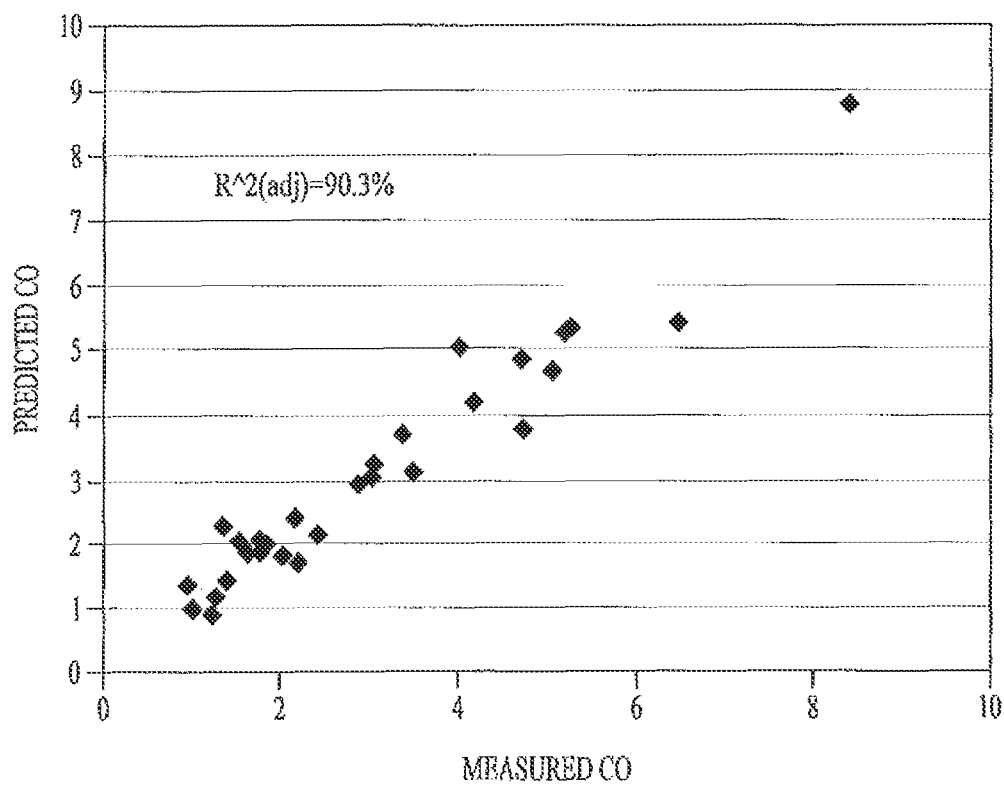
FIG. 9C illustrates generally an example of a comparison of single-feature, two-feature, and three-feature models.

FIG. 9C illustrates generally an example of a set of test data and corresponding adjusted $r^2$ values (or Mallow's Cp statistic). Adjusted $r^2$ can be used instead of a standard $r^2$ calculation to account for the inherent bias (i.e., a trend toward $r^2=1.0$) in the standard $r^2$ where multiple predictors are used. In the example of FIG. 9C, a single feature model for cardiac stroke volume 911 has a relatively poor correlation coefficient $r^2$ (i.e., the quantity of a least squares fitting to the original data) with a measured actual stroke volume. A single feature model for cardiac stroke volume 911 can, for example, be represented by equation (4). Using a two feature model for cardiac stroke volume 912 can improve $r^2$. Importantly, the choice of which waveform feature or features to use can have a significant impact on the correlation between the predictive model for cardiac stroke volume (e.g., SVsurgt[n]), and an actual measure of stroke volume.

A three feature model for cardiac stroke volume 913 can consistently yield $r^2$ values above 0.90, indicating a strong correlation between predicted (e.g., using equation (7)) and actual cardiac stroke volume. For example, FIG. 9D illustrates generally a chart 903 comparing measured cardiac output (that is, stroke volume multiplied by heart rate) on the x-axis and predicted cardiac output using the indication of a cardiac stroke volume, such as using equation (7), on the y-axis. The chart 903 indicates that the model for cardiac stroke volume is appropriate for accurately indicating an actual cardiac output.

Additional Notes & Examples

Example 1 can include subject matter, such as a medical device, comprising a processor or a processor circuit, including at least a first data input configured to receive, at multiple instances, a reference indication of a cardiac stroke volume from at least one physiological sensor, and a second data input configured to receive reference impedance information, at corresponding multiple instances, from at least one thoracic impedance vector, and configured to receive test impedance information from the same at least one thoracic impedance vector. Example 1 can include subject matter such as a processor-readable medium, including instructions that, when performed by the processor, configure the apparatus to: extract a reference waveform feature from the reference impedance information; determine a model for cardiac stroke volume using the reference waveform feature and the reference indication of cardiac stroke volume; extract a test waveform feature from the test impedance information; determine a test indication of a cardiac stroke volume using the test waveform feature and the model for cardiac stroke volume; and provide an indication of a cardiac status using the test indication of a cardiac stroke volume.

In Example 2, the subject matter of Example 1 can optionally include a processor circuit, including a first data input configured to receive test impedance information from at least one thoracic impedance vector, and a processor-readable medium, including instructions that, when performed by the processor, configure the apparatus to: extract a test waveform feature from the test impedance information; determine a test indication of a cardiac stroke volume using the test waveform feature and a model for cardiac stroke volume; and provide an indication of a cardiac status using the test indication of a cardiac stroke volume.

In Example 3, the subject matter of one or any combination of Examples 1-2 can optionally include a processor-readable medium including instructions that, when performed by the processor, can configure a medical device to determine a test indication of a cardiac stroke volume using a test waveform feature, the test waveform feature including at least one of: a heart rate discerned from the test impedance information; an amplitude of a portion of the test impedance information; an integral of a portion of the test impedance information; a mean amplitude of a portion of the test impedance information; a maximum derivative of a portion of the test impedance information; a ratio of features derived from the test impedance information; a linear combination of waveform features derived from the test impedance information; or a product of waveform features derived from the test impedance information, among others.

In Example 4, the subject matter of one or any combination of Examples 1-3 can optionally include a processor-readable medium including instructions that, when performed by the processor, can configure a medical device to provide an indication of a likelihood of heart failure, such as using a test indication of a cardiac stroke volume.

In Example 5, the subject matter of one or any combination of Examples 1-4 can optionally include a processor-readable medium including instructions that, when performed by the processor, can configure a medical device to provide an indication of cardiac remodeling, such as using a test indication of a cardiac stroke volume.

In Example 6, the subject matter of one or any combination of Examples 1-5 can optionally include a processor-readable medium including instructions that, when performed by the processor, can configure a medical device to provide an indication of a severity of a ventricular arrhythmia, such as using the test indication of a cardiac stroke volume.

In Example 7, the subject matter of one or any combination of Examples 1-6 can optionally include a first data input that can be configured to receive reference impedance information, such as at multiple instances, from at least one thoracic impedance vector. Example 7 can include a second data input configured to receive, at multiple instances, such as corresponding multiple instances, a reference indication of a cardiac stroke volume from at least one physiological sensor. Example 7 can include a processor-readable medium including instructions that, when performed by the processor, configure a medical device to extract a reference waveform feature from reference impedance information, and to determine a model for cardiac stroke volume using a reference waveform feature and a reference indication of a cardiac stroke volume.

In Example 8, the subject matter of one or any combination of Examples 1-7 can optionally include a third data input that can be configured to receive heart rate information, and a processor-readable medium including instructions that, when performed by the processor, can configure the medical device to determine the model for cardiac stroke volume, such as using the heart rate information.

In Example 9, the subject matter of one or any combination of Examples 1-8 can optionally include a second data input that can be configured to receive, at multiple instances, heart sound information that can be used to provide a reference indication of a cardiac stroke volume.

In Example 10, the subject matter of one or any combination of Examples 1-9 can optionally include a second data input that can be configured to receive, at multiple instances, impedance information indicative of a respiration status, such as can be used to provide a reference indication of a cardiac stroke volume.

In Example 11, the subject matter of one or any combination of Examples 1-10 can optionally include a second data input that can be configured to receive, at multiple instances, information indicative of a physical activity level that can be used to provide a reference indication of a cardiac stroke volume.

In Example 12, the subject matter of one or any combination of Examples 1-11 can optionally include a first data input that can be configured to receive test impedance information from at least one thoracic impedance vector at a first physical activity level, and a second data input that can be configured to receive, at multiple instances, a reference indication of a cardiac stroke volume using at least one physiological sensor, such as at a different second physical activity level.

In Example 13, the subject matter of one or any combination of Examples 1-12 can optionally include a first data input that can be configured to receive, over multiple cardiac cycles, test impedance information from at least one thoracic impedance vector, and a second data input that can be configured to receive, at multiple instances over multiple cardiac cycles, a reference indication of cardiac stroke volume, such as using at least one physiological sensor.

Example 14 can include, or can be combined with the subject matter of one or any combination of Examples 1-13 to optionally include subject matter such as a medical device, comprising a processor and a processor circuit, wherein the medical device can be configured to receive test impedance information from at least one thoracic impedance vector, extract a test waveform feature from the test impedance information, determine a test indication of a cardiac stroke volume using the test waveform feature and a model for cardiac stroke volume, and provide an indication of a cardiac status using the test indication of a cardiac stroke volume.

In Example 15, the subject matter of one or any combination of Examples 1-14 can optionally include determining a test indication of a cardiac stroke volume using the test waveform feature and a model for cardiac stroke volume, such as using at least one of: a heart rate discerned from the test impedance information; an amplitude of a portion of the test impedance information; an integral of a portion of the test impedance information; a mean amplitude of a portion of the test impedance information; a maximum derivative of a portion of the test impedance information; a ratio of features derived from the test impedance information; a linear combination of waveform features derived from the test impedance information; or a product of features derived from the test impedance information.

In Example 16, the subject matter of one or any combination of Examples 1-15 can optionally include providing an indication of a cardiac status using a test indication of a cardiac stroke volume, including providing at least one of: an indication of a likelihood of heart failure; an indication of cardiac remodeling; or an indication of a ventricular arrhythmia event.

In Example 17, the subject matter of one or any combination of Examples 1-16 can optionally include receiving, at multiple instances, a reference indication of a cardiac stroke volume from at least one physiological sensor, receiving reference impedance information, at corresponding multiple instances, from the at least one thoracic impedance vector, extracting a reference waveform feature from the reference impedance information, and determining the model for cardiac stroke volume using the reference waveform feature and the reference indication of cardiac stroke volume.

In Example 18, the subject matter of one or any combination of Examples 1-17 can optionally include receiving a reference indication of a cardiac stroke volume using at least one of heart rate information; heart sound information; impedance information indicative of a respiration status; or physical activity level information.

In Example 19, the subject matter of one or any combination of Examples 1-18 can optionally include receiving, at multiple instances, a reference indication of a cardiac stroke volume from at least one physiological sensor, including receiving, at multiple instances, the reference indication of a cardiac stroke volume from at least one physiological sensor at a first physical activity level and a second physical activity level, wherein the receiving test impedance information from the at least one thoracic impedance vector can include receiving test impedance information at a physical activity level that can be near the first and second physical activity levels.

In Example 20, the subject matter of one or any combination of Examples 1-19 can optionally include receiving, at multiple instances, a reference indication of a cardiac stroke volume from at least one physiological sensor, including receiving, at multiple instances over multiple cardiac cycles, the reference indication of a cardiac stroke volume from the at least one physiological sensor, wherein the receiving test impedance information from the at least one thoracic impedance vector can include receiving test impedance information from the at least one thoracic impedance vector over multiple cardiac cycles. These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and. B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline The claimed invention is:

1. An apparatus, comprising:
   a processor circuit, including:
      a first data input configured to receive reference impedance information and test impedance information from a thoracic impedance vector;
      a second data input configured to receive a reference indication of a cardiac stroke volume from at least one physiological sensor; and
   a processor-readable medium, including instructions that, when performed by the processor, configure the apparatus to:
      extract a test waveform feature from the test impedance information;
      extract a reference waveform feature from the reference impedance information;
      determine a model for cardiac stroke volume using the reference waveform feature and the reference indication of the cardiac stroke volume;
      determine a test indication of a cardiac stroke volume using the test waveform feature and the model for cardiac stroke volume; and
      provide an indication of a cardiac status using the test indication of a cardiac stroke volume.

2. The apparatus of claim 1, wherein the processor-readable medium includes instructions that, when performed by the processor, configure the apparatus to determine the test indication of cardiac stroke volume using the test waveform feature, the test waveform feature including at least one of:
   a heart rate discerned from the test impedance information;
   an amplitude of a portion of the test impedance information;
   an integral of a portion of the test impedance information;
   a mean amplitude of a portion of the test impedance information;
   a maximum derivative of a portion of the test impedance information;
   a ratio of features derived from the test impedance information;
   a linear combination of waveform features derived from the test impedance information; or
   a product of waveform features derived from the test impedance information.

3. The apparatus of claim 1, wherein the processor-readable medium includes instructions that, when performed by the processor, configure the apparatus to provide an indication of a likelihood of heart failure using the test indication of a cardiac stroke volume.

4. The apparatus of claim 1, wherein the processor-readable medium includes instructions that, when performed by the processor, configure the apparatus to provide an indication of cardiac remodeling using the test indication of a cardiac stroke volume.

5. The apparatus of claim 1, wherein the processor-readable medium includes instructions that, when performed by the processor, configure the apparatus to provide an indication of a severity of a ventricular arrhythmia using the test indication of a cardiac stroke volume.

6. The apparatus of claim 1, wherein:
   the first data input is configured to receive the reference impedance information at multiple instances, from the thoracic impedance vector; and
   the second data input is configured to receive the reference indication of the cardiac stroke volume at corresponding multiple instances.

7. The apparatus of claim 6, wherein the processor circuit includes a third data input configured to receive heart rate information; and
   wherein the processor-readable medium includes instructions that, when performed by the processor, configure the apparatus to determine the model for cardiac stroke volume using the heart rate information.

8. The apparatus of claim 6, wherein the second data input is configured to receive, at multiple instances, heart sound information that is used to provide the reference indication of a cardiac stroke volume.

9. The apparatus of claim 6, wherein the second data input is configured to receive, at multiple instances, impedance information indicative of a respiration status that is used to provide the reference indication of a cardiac stroke volume.

10. The apparatus of claim 6, wherein the second data input is configured to receive, at multiple instances, information indicative of a physical activity level that is used to provide the reference indication of a cardiac stroke volume.

11. The apparatus of claim 6, wherein:
    the first data input is configured to receive the test impedance information, from at least one thoracic impedance vector, at a first physical activity level; and
    the second data input is configured to receive, at multiple instances, the reference indication of cardiac stroke volume from the at least one physiological sensor at a different second physical activity level.

12. The apparatus of claim 6, wherein the first data input is configured to receive, over multiple cardiac cycles, the test impedance information from the at least one thoracic impedance vector; and
    wherein the second data input is configured to receive, at multiple instances over multiple cardiac cycles, the reference indication of cardiac stroke volume from the at least one physiological sensor.

13. A method comprising:
    receiving a reference indication of a cardiac stroke volume from at least one physiological sensor;
    receiving reference impedance information from at least one thoracic impedance vector;
    extracting a reference waveform feature from the reference impedance information;
    determining a model for cardiac stroke volume using the reference waveform feature and the reference indication of cardiac stroke volume;
    receiving test impedance information from the at least one thoracic impedance vector;
    extracting a test waveform feature from the test impedance information;
    determining a test indication of a cardiac stroke volume using the test waveform feature and the model for cardiac stroke volume; and
    providing an indication of a cardiac status using the test indication of a cardiac stroke volume.

14. The method of claim 13, wherein the determining a test indication of a cardiac stroke volume using the test waveform feature and a model for cardiac stroke volume includes using at least one of:

a heart rate discerned from the test impedance information;
an amplitude of a portion of the test impedance information;
an integral of a portion of the test impedance information;
a mean amplitude of a portion of the test impedance information;
a maximum derivative of a portion of the test impedance information;
a ratio of features derived from the test impedance information;
a linear combination of waveform features derived from the test impedance information; or
a product of features derived from the test impedance information.

15. The method of claim 13, wherein the providing an indication of a cardiac status using the test indication of a cardiac stroke volume includes providing at least one of:
an indication of a likelihood of heart failure;
an indication of cardiac remodeling; or
an indication of a ventricular arrhythmia event.

16. The method of claim 13, wherein the receiving the reference indication of a cardiac stroke volume includes at multiple instances, and
wherein the receiving the reference impedance information includes at corresponding multiple instances.

17. The method of claim 16, wherein the receiving the reference indication of a cardiac stroke volume includes using at least one of:
heart rate information;
heart sound information;
impedance information indicative of a respiration status; or
physical activity level information.

18. The method of claim 16, wherein the receiving, at multiple instances, a reference indication of a cardiac stroke volume from at least one physiological sensor includes receiving, at multiple instances, the reference indication of a cardiac stroke volume from the at least one physiological sensor at a first physical activity level and a second physical activity level; and
wherein the receiving test impedance information from the at least one thoracic impedance vector includes receiving test impedance information at a physical activity level that is near the first and second physical activity levels.

19. The method of claim 16, wherein the receiving, at multiple instances, a reference indication of a cardiac stroke volume from at least one physiological sensor includes receiving, at multiple instances over multiple cardiac cycles, the reference indication of a cardiac stroke volume from the at least one physiological sensor; and
wherein the receiving test impedance information from the at least one thoracic impedance vector includes receiving test impedance information from the at least one thoracic impedance vector over multiple cardiac cycles.

* * * * *